United States Patent [19]
Thomas

[11] 4,094,916
[45] June 13, 1978

[54] PROCESS FOR THE PRODUCTION OF ENDO-ENDO HEXACYCLIC DIMER OF NORBORNADIENE

[75] Inventor: Jeffrey R. Thomas, Aston, Pa.

[73] Assignee: Suntech, Inc., Wayne, Pa.

[21] Appl. No.: 767,600

[22] Filed: Feb. 10, 1977

[51] Int. Cl.$^2$ .............................................. C07C 1/00
[52] U.S. Cl. ........................ 260/666 A; 260/666 PY; 60/219
[58] Field of Search .................... 260/666 A, 666 PY; 60/219

[56] References Cited

U.S. PATENT DOCUMENTS 3,703,361  11/1972  Konecky ............................ 60/215 X Primary Examiner—Stephen J. Lechert, Jr.
Attorney, Agent, or Firm—J. Edward Hess; Donald R. Johnson; Anthony Potts, Jr.

[57] ABSTRACT

Process involves the continuous production of endo-endo stereoisomer of the hexacyclic dimer of norbornadiene using a three component catalystic system of diethylaluminum chloride, ferric acetylacetonate and triphenylphosphino. Temperature range of reaction is about 100°–200° F and residence time is about 1–10 hours. Process further involves taking a product stream, along with any catalyst and other materials, and treating it to deactivate the catalyst; then separating the desired endo-endo dimer by various means at a temperature below about 500° F to avoid decomposition of iron salts. Unreacted norbornadiene is recycled.

7 Claims, 1 Drawing Figure

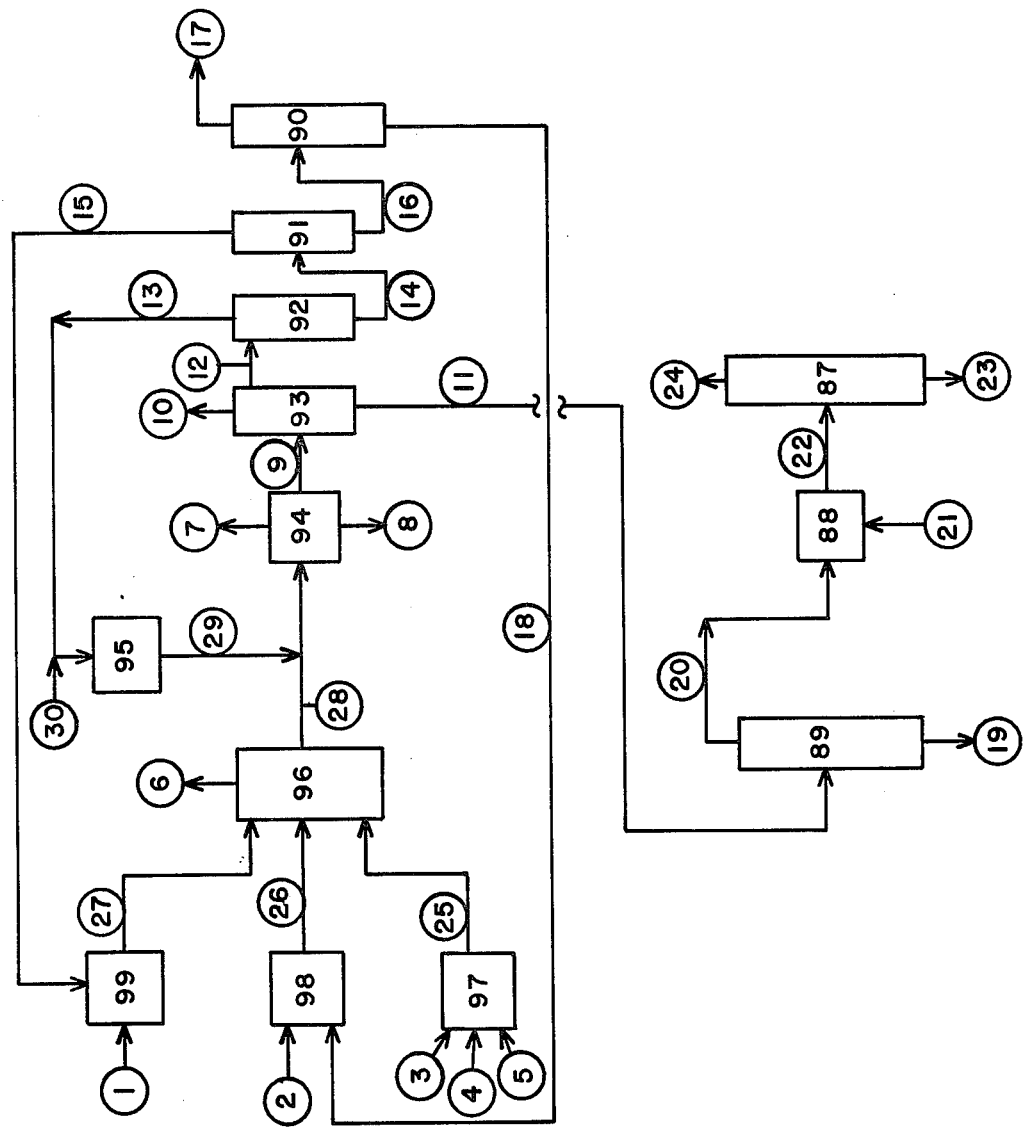

PROCESS FOR THE PRODUCTION OF ENDO-ENDO HEXACYCLIC DIMER OF NORBORNADIENE

CROSS REFERENCES

This application is related to the subject matter in assignee's U.S. patent application Ser. No. 640,102, filed Mar. 29, 1976.

BACKGROUND OF THE INVENTION

The invention herein described was made in the course of or under a contract thereunder with the U.S. Air Force Systems Command.

This invention generally relates to a process for the dimerization of norbornadiene. In particular, the invention relates to producing a hydrocarbon mixture having a high concentration of a monoolefinic hexacyclic hydrocarbon known by the systematic chemical name of endo-endo stereoisomer of hexacyclo(7.2.1.0$^{2,8}$.1$^{3,7}$.1$^{5,13}$.0$^{4,6}$)tetradec-10-ene (also designated as hexayclo[9.2.1.0$^{2,10}$.0$^{3,8}$.0$^{4,6}$.0$^{5,9}$]-tetradec-12-ene). The stereoisomer results from the catalytic dimerization of norbornadiene which is a $C_7H_8$ bicyclic, diolefinic hydrocarbon. More particularly, the invention relates to a process for producing a mixture of a high concentration of the endo-endo form of the hexacyclic dimer. The latter is a $C_{14}H_{16}$, six-ring monoolefinic hydrocarbon. The process can be continuous and has an advantage of recycling certain streams thereby reducing costs and increasing yields. Also, the invention relates to a process in which the product has been hydrogenated to convert the monoolefinic hexacyclic hydrocarbon to a completely saturated hexacyclic hydrocarbon. Hydrogenation of a monoolefinic hexacyclic dimer to a staturated dimer improves stability of the product towards oxidation thereby enhancing its utility as a high energy fuel. Completely saturated endo-endo hexacyclic dimer has a utility as a component of high energy fuel.

An object of present invention is to provide an ecnomical process which can produce a compositon which has a maximum concentration of hexacyclic norbornadiene dimers and other compounds. Also the composition can be used as a component of a high energy fuel for use in either jet or rocket propulsion. Jet propulsion includes a jet engine which can be used for missile, plane and other applications and includes the three basic types, i.e., ramjet, turbo-jet and pulse jet. The term jet generally refers to a device requiring air whereas rocket generally refers to a device containing its own oxygen or oxidizing agent.

Norbornadiene is also known as bicyclo-(2.2.1) heptadiene-2,5. A method of preparation is disclosed in U.S. Pat. No. 2,875,256 issued Feb. 24, 1959. Norbornadiene is referred to as NBD hereinafter. NBD can be represented by either one of the following structural formulas:

 or 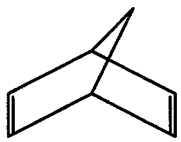

Dimerization of NBD is disclosed in U.S. Pat. No. 3,377,398, issued Apr. 9, 1968. The disclosed process results in the production of various dimer mixtures. The process therein involves the use of an iron catalyst system, e.g., ferric acetylacetonate and triethylaluminum, and a temperature above 140° C. The product of said method is a mixture which includes both monoolefinic hexacyclic and diolefinic pentacyclic dimers.

U.S. Pat. No. 3,282,663, issued Nov. 1, 1966, also discloses the dimerization of NBD to pentacyclic and hexacyclic dimers. In one example, tetrakis(triphenylphosphine)nickel is the catalyst, in another, ferric acetylacetonate and treithylaluminum is the catalyst. One of the dimers reported therein, i.e., Dimer III, has been identified as the endo-endo sterioisomer of the hexacyclic dimer of norbonadiene.

U.S. Pat. No. 3,326,922, issued June 20, 1967, discloses the partial hydrogenation of NBD dimer mixtures.

U.S. Pat. No. 3,326,993, issued June 20, 1967, discloses the dimerization of NBD in the presence of certain cobalt based catalysts to heptacyclic dimers. The resulting dimer mixture contains major proportion of the completely saturated dimer.

U.S. Pat. No. 3,329,732, issued July 4, 1967, discloses an improved method for the dimerization of NBD. The catalyst comprises certain metal salts of the tetracarbonylcobaltate anion wherein the metal is zinc, cadmium, mercury or indium. Resulting dimer mixture contains predominantly hexacyclic NBD dimers.

Catalytic reaction of NBD and butadiene is disclosed in an article in The Journal of Organic Chemistry, January, 1970, Vol. 35, titled "Catalytic Norbornadiene-Butadiene and Norbornadiene-1,1-Dimethylallene Codimerization," by A Greco et al., pages 271–274. One of the disclosed catalysts is a three component system of tris(acetylacetonate)iron-AlEt$_2$Cl-bis(diphenylophosphine) ethane. AlEt$_2$Cl refers to diethylaluminum chloride. One of the dimers reported therein, i.e., FIG. 1e, has been identified as the exo-exo stereoisomer of the hexacyclic dimer of norbornadiene.

Also, a catalystic reaction of NBD is disclosed in an article in The Journal of the American Chemical Society, Vol. 94, July 26, 1972, starting page 5446, titled "Dimerization and Trimerization of Norbornadiene by Soluble Rhodium Catalyst," by Nancy Acton et al. This article discloses the endo-endo form of the hexacyclic dimer of NBD.

As the previous discussion indicates, more than one NBD dimer is possible. G. N. Schzauzer, in his review "On Transitiron Metal-Catalyzed Reactions of Norbornadiene and the Concept of a Complex Multicenter Processes" in Advances on Catalysis 18,373 (1968) Acad. Press, describes the fourteen theoretically possible dimers of NBD.

Thus, a specific process problem in the dimerization of NBD, as can be visualized from the number of possible isomers, is to obtain substantial amounts of the endo-endo isomer at high yields and at reduced costs. Also the problem is to minimize the production of pentacyclics. The latter are not desirable as high energy fuels because of their high melting points and separation of pentacyclic dimers from the hexacyclic dimers is commercially not feasible at this time. On the other hand the desired endo-endo hexacyclic dimer can be readily separated from small amounts of unreacted feed and other products, particularly higher boiling polymers. Hydrogenation of the endo-endo material provides a material which can be used as a component for high energy, high density fuel.

The advantages of present invention are many. The process can be continuous. Recycling of various streams, without build up of unwanted by-products within the process, reduces costs and increases yields.

SUMMARY OF THE INVENTION

The process involves the dimerization of NBD to the endo-endo form of the $C_{14}H_{16}$ hexacyclic dimer. The process requires an amount of a three component catalytic system of diethylaluminum chloride, ferric acetylacetonate and triphenylphosphine sufficient to dimerize the NBD. The three components of the catalytic system are referred to hereinafter as DEAC, $Fe(A)_3$, and TPP respectively. Also the process requires a temperature between the range of from about 100° to about 200° F and sufficient residence contacting time to obtain the desired amount of endo-endo hexacyclic dimer.

A product mixture stream, along with any catalyst, is removed from contacting and treated to deactivate the catalyst. The product mixture is separated from the deactivated catalyst and any other material and then the endo-endo hexacyclic dimer is obtained by separation means such as distillation from the treated product mixture. The separation steps occur at a temperature below about 500° F otherwise an iron salt decomposes and contaminates the desired dimer. Recycle of unreacted NBD, along with other materials, also occurs.

DESCRIPTION OF THE DRAWING

The accompanying drawing schematically illustrates one embodiment of carrying out the dimerization of NBD to its endo-endo hexacyclic dimer and the hydrogenation of the dimer according to the invention.

DESCRIPTION OF THE INVENTION

One embodiment of the invention is hereinafter described in connection with the drawing.

The feed 1, consisting essentially of NBD, is fed to a surge device, 99 e.g. a tank. The feed is then moved to contacting means, 96 e.g. a reaction vessel. In a similar fashion DEAC 2, usually dissolved in an aromatic solvent such as toluene, is fed to a surge device 98 and then moved to the contacting means 96. Also, $Fe(Ac)_3$ 3 and TPP (4) are fed to a surge device 97 to which is also fed NBD 5 which acts as a solvent for the $Fe(Ac)_3$ and TPP. Other suitable solvents can be used. The resulting mixture 25 of NBD 5 and $Fe(Ac)_3$ and TPP 4 is fed to contacting means 96.

Contacting means 96 can contain agitation means, not shown, and can be equipped with sufficient heating and/or cooling means, not shown, to control the temperature of the contacting mixture. The capacity of the means 96 depends on the flow rate of the feed 27 and desired residence time. Residence time is defined as the volume of the contacting means 96 divided by the rate, i.e., the total volume/hour, of the materials, i.e., the 27, 26 and 25, entering the contacting means 96.

Within the confines of the contacting means 96 the dimerization of the NBD to the unsaturated endo-endo hexacyclic dimer along with other polymers occurs. During the contacting the contacting mixture can be stirred and the temperature controlled within an operable range. During the contacting gases, 6 such as ethylene and/or hydrogen, can evolve. The gases can be consumed as fuel or recovered and used elsewhere. The dimerization of NBD can also be referred to as the reaction of NBD to form dimers.

Since the process can be continuous, the feed 27, DEAC 26 and catalyst mixture 25 are fed continuously to the contacting means 96 and a product mixture is continuously removed. The removed product mixture 28 is treated with a deactivator 29 e.g. an alcohol such as methanol or water. The deactivator 29 deactivates any DEAC, $Fe(Ac)_3$ and TPP which requires deactivation. After the deactivation, a sludge 8 containing aluminum hydroxide, alkyl aluminum hydroxide, insoluble polymers, and like materials is separated via separating means 94 e.g. filter device. Also during the separation some gases 7 can evolve and which can be referred to as an offgas 7.

The treated product mixture, 9 no longer containing the sludge, is separated in separation means 93 e.g. a distillation tower. Critical to this step is that the temperature occuring during e.g. the ditillation and in particular the bottoms temperature, not exceed 500° F. If a higher temperature is used decomposition of an iron salt occurs and the decomposition product or products can contaminate the desired dimer. From means 93 e.g., distillation tower, a distillate 12, a overhead 10 and a bottoms 11 are obtained. The overhead 10 contains hydrocarbons and is often referred to as light ends. The distillate 12 contains the deactivator e.g. methanol or water, unreacted NBD and any solvent e.g. toluene, used with the DEAC. The bottoms 11 contains the desired dimer, by-product polymers formed during the contacting, an iron salt, TPP and other like materials. The iron salt, TPP and other like materials are often referred to as residue.

The distillate 12 can be further processed by feeding it to another separating means 92 e.g. a distillation device. With a distillation device an overhead 13 of methanol and/or water can be obtained and the overhead can be sent to surge means 95 along with makeup material 30. A stream of deactivator 29 can be obtained from surge means 95 and can be used to treat the product mixture 28.

From separating means 92 a bottoms 14 is obtained and fed to separating means 91, e.g. a distillation device. The bottoms 14 contains unreacted NBD and solvent, if any, used with the DEAC. In separating means 91 the unreacted NBD is taken as an overhead (15) and returned to surge device 99 or to a suitable storage, not shown. In surge device 99 the recycled unreacted NBD is mixed with fresh NBD 1 and becomes a portion of feed 27. The bottoms 16 from separating means 91, is sent to another separating means 90, e.g. a distillation device, where any solvent, if used, is taken as bottoms 18 and returned to surge means 98 for reuse or to a suitable storage, not shown. In surge device 98 the recycled solvent is mixed with the DEAC and becomes a portion of feed 26. From separating means 90 an overhead 17 is obtained, the latter is referred to as slop and is any material which was carried unwanted through the previous separating means.

The bottoms 11 from the separating means 93, containing the desired dimer, by-product polymers, iron salt, TPP and other like materials, is fed to separating means 89 e.g. a distillation device. An example of the latter is vacuum distillation. Critical to this step is that the temperature occurring during the distillation, and in particular the bottoms temperature, not exceed 500° F. If a higher temperature is used decomposition of an iron salt occurs and the decomposition product or products can contaminate the desired dimer. Separating means 89 effectuates the separation of the bottoms 11 into a bottoms 19 and an overhead 20. The bottoms 19 having an initial boiling point in excess of about 550° F, contains the other polymers formed and any unwanted residue. The bottoms 19 are disposed of in a suitable manner.

The overhead 20 contains the desired dimer and has a boiling range of about 450° to about 550° F. Because the desired dimer is unsaturated the overhead (20) is fed to hydrogenation means 88, along with hydrogen 21, and hydrogenated using a typical hydrogenation catalyst such as nickel on kieselguhr. During the hydrogenation the temperature generally does not exceed about 75° C and the hydrogen is present at about 150 psig.

The hydrogenated product 22 from the hydrogenation means 88 is sent to a separating means 87 e.g. a distillation device, to remove light ends 24, e.g., hydrogen and light hydrocarbons, if any. The bottoms 23 from the separating means 87 is the desired saturated endo-endo hexacyclic dimer.

The catalytic dimerization of NBD via present invention can be represented by the following formula reaction:

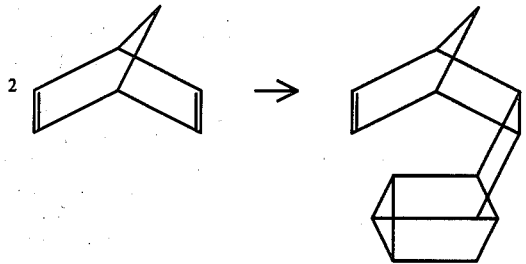

The dimerization requires an amount of DEAC, Fe-(Ac)$_3$ and TPP sufficient to dimerize the NBD.

The feed to present invention consists essentially of NBD. Other hydrocarbons and in particular unsaturated hydrocarbons which could react with NBD or adversly effect the catalyst and/or DEAC should be excluded. However the feed can contain minor amounts of the precursors, such as cyclopentadiene, used to make the NBD. The feed can also contain other nonreactive hydrocarbons such as toluene and benzene. Small amounts of inhibitors such as 2,6-di-t-butyl-4-methylphenol, can be present. They inhibit formation of explosive peroxides. Very small amounts of water, e.g. about 100 ppm, can be tolerated, however, too much water can adversely effect the reaction.

The amount of DEAC, Fe(Ac)$_3$ and TPP present in the contacting zone is an effective amount so that a suitable conversion to the desired dimer occurs and the selectivity is sufficient. Any material which during the contacting could adversely effect the catalyst mixture and/or DEAC should not be present. For example, the presence of hydroxylic compounds such as water, alcohol or oxygen from air could deactivate the catalyst mixture and/or DEAC. The concentration of the Fe-(Ac)$_3$ during the contacting can vary substantially but generally will be between the range from about 0.01 to about 0.1 gram moles per liter of contacting space; a preferred range is from about 0.02 to about 0.8. The concentration of the TPP can also vary but generally is related to the amount of the Fe(Ac)$_3$ present, generally, its mole ratio to Fe(Ac)$_3$ will be between from about 1:1 to about 10:1 a preferred ratio of TPP to Fe(Ac)$_3$ range is between from about 2:1 to about 8:1. The concentration of the DEAC can vary but generally its concentration during the contacting will be between the range from about 0.2 to about 1.0 gram moles per liter of contacting space; a preferred range is from about 0.3 to about 0.8.

During the contacting the temperature generally will be between the range of from about 100° F to about 200° F. If a higher temperature is used the reaction could result in an uncontrolled exotherm or an undesirable amount of unwanted by-products could be made. If a lower temperature is used the reaction could be so slow as to be economically unattractive. However, within the general temperature range of about 100° to about 200° F, a higher temperature can be used to lower the residence time with the contacting zone. A preferred temperature range is from about 120° to about 180° F.

During the contacting the pressure can vary substantially; however, generally it will be in the range between from about atmospheric to about 500 psig. Pressure can help reduce the gases generated during the contacting and also facilitate the handling of any gas that does evolve. However, higher pressure can result in increased operating costs and equipment investments and thus should be minimized as long as the problems created do not offset the savings.

The residence time for the contacting depends on the volume rates of the materials fed to the contacting zone, the volume of the contacting zone, and the temperature and pressure of the contacting. Thus the residence time can vary substantially. Generally it will be between the range from about one hour to about 10 hours with a preferred range of from two hours to about eight hours.

Conversion of the NBD to the dimers depends on the aforementioned temperature range, concentrations of catalyst, the amount of agitation, residence time and other such variables. While it is desirable from an economic consideration to obtain as high a conversion as possible it is possible to optimize conversion in terms of selectivity, and minimizing unwanted by-products, catalyst life and the like. Generally; however, the conversion of NBD to dimer will be in excess of 50%, preferably in excess of 75%. The variables effecting the conversion also effect the selectivity of the NBD to the endo-endo dimer. Generally the selectivity will be in excess of 70%, preferably in excess of 80%.

The product mixture, removed from the contacting zone and which can be cooled, contains the desired endo-endo hexacyclic dimer along with the Fe(Ac)$_3$, TPP and DEAC, and other materials. To deactivate the product mixture an alcohol such as methanol can be used. Equally effective is water including salt water. As a result of the deactivation a sludge is formed. The sludge is an undefined mixture but may include aluminum hydroxide, alkyl aluminum hydroxide, water, and other materials. And the sludge can be removed by such methods as filtration.

The treated contacting product mixture, after separation of the sludge, still contains an undefined iron salt. Thus it is critical that the product mixture not reach a temperature which will decompose the salt.

Decomposition of the salt results in materials which contaminate the desired dimer product. Generally, the maximum temperature is believed to be about 500° F; however, a preferred maximum temperature is about 475° F with 450° F more preferred.

After the separation of the unwanted materials desired endo-endo product can have a different boiling rante depending on the sharpness of the preceding separation steps. Generally, the products boiling range will be about from about 440° F to about 560° F; however, with sharper separation steps the preferred boiling range will be from about 450° F to about 550° F.

Because the desired endo-endo product is olefinic it is hydrogenated. The hydrogenation takes place in the presence of hydrogen and a hydrogenation catalyst such as nickel on kieselguhr, ruthenium on carbon, palladium on carbon, platinum oxide, palladium on alumina, ruthenium on alumina and others. The hydrogenation is generally complete so that essentially no unsaturation remains. The purpose of the hydrogenation is to replace the double bond with hydrogen thereby minimizing product degradation while the product is in storage. The hydrogenation temperature and pressure can vary substantially and depend on part of the selected catalysts and decomposition temperature of the product.

The following examples serve to further illustrate applicant's invention.

EXAMPLES

The following described procedure was generally used to obtain the data reported in the accompanying table.

Three storage containers were purged with nitrogen. DEAC, 25% by weight, dissolved in toluene, was charged to one container. The desired weights of FE-(Ac)$_3$ and TPP were measured and charged to a preparation container. The charged materials were then diluted with sufficient NBD to obtain the following ratios: for Fe(Ac)$_3$ 73.6 mg/cc of NBD; for TPP 218.3 mg/cc. The resulting mixture was warmed to facilitate the dissolving of the TPP, however, some insolubles, about 0.2 wt. % of the solids charged were removed by filtration. The insolubles were believed to be impurities. The filtered mixture was then charged to another container. NBD, commercially available at 97 weight % purity, was charged to another container. The impurities in the NBD were as follows: dicyclopentadiene 1 wt. %, cycloheptatriene 1.2 wt. %, toluene 0.1 wt. %, benzene 0.1 wt. %, other 0.1 wt. %, inhibitor (2,6-di-t-butyl-4-methylphenol) 0.05 wt. %. After charging the three storage containers were kept under nitrogen at a pressure of about 170 psig. The latter pressure was sufficient to maintain the desired flow rate to the reactor. The Fe(Ac)$_3$, TPP and DEAC were of commercial quality.

A reaction reactor was dried and purged with nitrogen. Product receivers, vessels which would receive product from the reactors, were charged with methanol to deactivate the active materials. With runs 15 and 16, water was satisfactorly used to deactivate the active materials. NBD was fed from its container to the reaction reactor and its rate measured by a rotameter. Once the reaction reactor was filled the NBD was fed at a rate to obtain the desired residence time and NBD/TPP/DEAC/Fe(Ac)$_3$ ratios. Then the DEAC solution and the FE(Ac)$_3$/TPP mixture were fed from their respective containers to the reaction reactor. For runs made with a residence time of 4 hours, initially the solution and the mixture were fed at a rate twice the maintenance rate for about the first 2–3 hours. Maintenance rate is that rate which maintains the desired concentration of materials in the reactor and obtains the desired residence time in the reaction reactor. The rates were measured by a rotameter. After the first 2–3 hours the flow rates were reduced to a desired maintenance rate.

During the foregoing the temperature of the materials in the reactor was heated to the desired level by suitable heating means. Also mixing means within the reaction reactor maintained good mixing.

Throughout the runs flow rates and temperature were controlled at the desired levels. Samples of reactor product were analyzed by gas chromatography (GC). When two consecutive samples gave analyses which agreed within 5% on dimer conversion the unit was considered to be lined out and thus the start up period was over.

At the end of the run the product in the product receiver was separated from the methanol or water and deactivation sludge. Samples of the product were analyzed by G.C. Selectivities and conversions were calculated based on the foregoing analyses. The aforementioned results and the operating conditions are given in the accompanying Table.

Comparison of Runs 1–16 indicate that % conversions to dimer as high as 95.8% were obtained. The same runs also indicate that selectivities as high as 86.8% were obtained. In particular, Run 14 indicates that a good conversion and a good selectivity can be achieved with only traces of byproducts e.g. trimer and heavier. Runs 15 and 16 indicate that good conversion is obtainable at temperatures as low as about 125° F. Run 10 indicates that an effective amount of DEAC must be present or otherwise the conversion is inadequate. The endo-endo product can then be processed as heretofore disclosed through units 93, 89, 88 and 87. Other streams can also be processed as heretofore disclosed through units 92, 91 and 90.

Analogous conversions and selectivities can be obtained when other temperatures then those reported are used, or other concentrations of Fe(Ac)$_3$ and DEAC are used; or other mole ratios of TPP/Fe(Ac)$_3$ are used.

TABLE

CONTINUOUS DIMERIZATION OPERATING CONDITIONS AND RESULTS

| RUN | Residence Time Hours | Concentration of Fe(Ac)$_3$ Mole per Volume of Reactor | Mole Ratio of TPP/Fe(Ac)$_3$ | Concentration of DEAC Mole per Volume of Reactor | Reactor Temperature °F | Reactor Pressure psig | Length of Run Hours | % Conversion to Dimer | % Selectivity Endo-Endo Dimer | % Conversion to Trimer & Heavier |
|---|---|---|---|---|---|---|---|---|---|---|
| 1 | 2 | 0.05 | 4:1 | 0.5 | 160 | 150 | 5 | 52 | (a) | (a) |
| 2 | 2 | 0.05 | 4:1 | 0.5 | 140 | 150 | 3 | 80 | (a) | (a) |
| 3 | 2 | 0.03 | 4:1 | 0.3 | 160 | 150 | 5 | 57 | (a) | (a) |
| 4 | 2 | 0.03 | 4:1 | 0.3 | 160 | 150 | 15 | 55 | (a) | (a) |
| 5 | 2 | 0.04 | 4:1 | 0.3 | 160 | 150 | 2 | — | (a) | (a) |
| 6 | 2 | 0.04 | 4:1 | 0.3 | 160 | 150 | 10 | 38 | (a) | (a) |
| 7 | 2 | 0.04 | 4:1 | 0.3 | 160 | 150 | 14 | 28 | 81 | 3.5 |
| 8 | 4 | 0.05 | 4:1 | 0.3 | 160 | 150 | 6 | 66 | (a) | (a) |
| 9 | 4 | 0.03 | 4:1 | 0.3 | 160 | 150 | 8 | 82 | (a) | (a) |
| 10 | 4 | 0.03 | 4:1 | 0.15 | 140 | 150 | 9 | nil | (a) | (a) |
| 11 | 4 | 0.03 | 4:1 | 0.3 | 160 | 150 | 12 | 90 | 84 | (a) |
| 12 | 4 | 0.03 | 4:1 | 0.3 | 160 | 150 | 6 | 91 | 85.2 | (a) |
| 13 | 4 | 0.03 | 4:1 | 0.3 | 160 | 150 | 13 | 95.8 | 86.5 | (a) |

TABLE-continued
CONTINUOUS DIMERIZATION OPERATING CONDITIONS AND RESULTS

| RUN | Residence Time Hours | Concentration of Fe(Ac)$_3$ Mole per Volume of Reactor | Mole Ratio of TPP/Fe(Ac)$_3$ | Concentration of DEAC Mole per Volume of Reactor | Reactor Temperature °F | Reactor Pressure psig | Length of Run Hours | % Conversion to Dimer | % Selectivity Endo-Endo Dimer | % Conversion to Trimer & Heavier |
|---|---|---|---|---|---|---|---|---|---|---|
| 14 | 4 | 0.03 | 4:1 | 0.3 | 165 | 150 | 12 | 92.5 | 86.8 | trace |
| 15 | 5.7 | 0.03 | 4:1 | (b) | 124 | 30 | — | 85 | (a) | (a) |
| 16 | 6.5 | 0.03 | 4:1 | (b) | 126 | 26 | — | 83 | (a) | (a) |

(a)No data.
(b)In runs 15 and 16 the mole ratio of DEAC/Fe(Ac)$_3$ was 15:1 and 14:1 respectively.

The invention claimed is:

1. Process for the dimerization of norbornadiene to its endo-endo hexacyclic dimer and hydrogenation of the dimer comprising:
    (a) contacting a feed consisting essentially of norbornadiene with diethylaluminum chloride and a catalyst mixture of ferric acetylacetonate and triphenylphosphine at a temperature between the range of from about 100° F to about 200° F and at a pressure between the range of from about atmospheric to about 500 psig and the amount of both the diethylaluminum chloride and the catalyst mixture is sufficient to dimerize the norbornadiene to the endo-endo hexacyclic dimer;
    (b) maintaining the contacting for a residence time sufficient to form the endo-endo hexacyclic dimer;
    (c) removing from the contacting a product mixture containing the formed endo-endo hexacyclic dimer and treating the mixture with methanol or water to deactivate the diethylaluminum chloride and the catalyst mixture;
    (d) separating from the treated contacting product mixture aluminum hydroxide sludge formed during the deactivation;
    (e) distilling the treated contacting product mixture from which the sludge was removed at a temperature below about 500° F to obtain both a distillate mixture and a bottom mixture wherein the distillate mixture contains any methanol or water not reacted during deactivation, unreacted norbornadiene and any solvent used with the diethylaluminum chloride; and the bottom mixture contains the endo-endo hexacyclic dimer, and other polymers formed during the contacting and any residue from the ferric acetylacetonate, triphenylphosphine, and the diethylaluminum chloride;
    (f) vacuum distilling the bottoms mixture at a temperature below about 500° F to obtain both a distillate and bottoms and wherein the distillate has a boiling range of about 440° to about 560° F and the bottoms has an initial boiling point of about 550° F and contains the other polymers formed and any residue; and
    (g) hydrogenating the about 550° F to about 550° F distillate so that essentially no unsaturation of the distillate containing the endo-endo hexacyclic dimer remains.

2. Process according to claim 1 wherein the distillate mixture of step (e) is further distilled so that the separated methanol or water, can be recycled to deactivate the diethylaluminum chloride and catalyst while the unreacted norbornadiene can be recycled to the contacting step (a), and any solvent used with the diethylaluminum chloride can be recycled to dilute the diethylaluminum chloride used in step (a).

3. Process according to claim 1 wherein the concentration of the ferric acetylacetonate during the contacting is between the range from about 0.01 to about 0.1 gram moles per liter of contacting space and the mole ratio of the phosphine to ferric acetylacetonate is between the range from about 1:1 to about 10:1 and the concentration of the diethylaluminum chloride during the contacting is between the range from about 0.2 to about 1.0 gram moles per liter of contacting space.

4. Process according to claim 1 wherein the conversion of norbornadiene to dimers is in excess of 50%.

5. Process according to claim 1 wherein the selectivity to the endo-endo hexacyclic dimer is in excess of 70%.

6. Process according to claim 5 wherein the distillate mixture step (e) is further distilled so that the separated methanol or water can be recycled to deactivate the diethylaluminum chloride and catalyst, the unreacted norbornadiene can be recycled to the contacting of step (a), and any solvent used with the diethylaluminum chloride can be recycled to dissolve the diethylaluminum chloride used in step (a).

7. Process according to claim 6 wherein the concentration of the ferric acetylacetonate during the contacting is between the range from about 0.01 to about 1.0 gram moles per liter of contacting space and the mole ratio of the phosphine to ferric acetylacetonate is between the range from about 1:1 to about 10:1 and the concentration of the diethylaluminum chloride during the contacting is between the range from about 0.2 to about 1.0 gram moles per liter of contacting space.

* * * * *